US012714096B2

(12) United States Patent
Matsusaki et al.

(10) Patent No.: US 12,714,096 B2
(45) Date of Patent: Aug. 25, 2026

(54) METHOD FOR FREEZING CELL STRUCTURE

(71) Applicants: OSAKA UNIVERSITY, Suita (JP); TOPPAN Holdings Inc., Tokyo (JP); Kyoto Prefectural Public University Corporation, Kyoto (JP)

(72) Inventors: Michiya Matsusaki, Suita (JP); Fiona Louis, Suita (JP); Shiro Kitano, Tokyo (JP); Yoshihiro Sowa, Kyoto (JP)

(73) Assignees: OSAKA UNIVERSITY, Osaka (JP); TOPPAN HOLDINGS INC., Tokyo (JP); KYOTO PREFECTURAL PUBLIC UNIVERSITY CORPORTION, Kyoto (JP)

( * ) Notice: Subject to any disclaimer, the term of this patent is extended or adjusted under 35 U.S.C. 154(b) by 472 days.

(21) Appl. No.: 18/250,814

(22) PCT Filed: Oct. 15, 2021

(86) PCT No.: PCT/JP2021/038303

§ 371 (c)(1),
(2) Date: Apr. 27, 2023

(87) PCT Pub. No.: WO2022/091822

PCT Pub. Date: May 5, 2022

(65) Prior Publication Data

US 2023/0389540 A1 Dec. 7, 2023

(30) Foreign Application Priority Data

Oct. 29, 2020 (JP) ................................ 2020-181512

(51) Int. Cl.
*A01N 1/162* (2025.01)
*C12N 5/0775* (2010.01)

(52) U.S. Cl.
CPC ........... *A01N 1/162* (2025.01); *C12N 5/0667* (2013.01); *C12N 2533/56* (2013.01)

(58) Field of Classification Search
CPC ...... A01N 1/162; C12N 5/0667; C12N 5/069; C12N 2502/1382; C12N 2502/28; C12N 2533/56; C12N 1/04; C07K 14/745
See application file for complete search history.

(56) References Cited

U.S. PATENT DOCUMENTS

2011/0177593 A1 7/2011 Funaki et al.
2013/0236429 A1 9/2013 Melero-Martin et al.
2018/0117217 A1 5/2018 Lee et al.
2018/0361025 A1 12/2018 Lancaster et al.
2020/0086007 A1 3/2020 Thomson et al.

FOREIGN PATENT DOCUMENTS

| | | | |
|---|---|---|---|
| CN | 113677700 A | 11/2021 | |
| JP | 2019-004904 | 1/2019 | |
| JP | 2019-528765 | 10/2019 | |
| JP | 2020-524002 | 8/2020 | |
| WO | WO 2015/072164 A1 | 5/2015 | |
| WO | WO 2017/146124 A1 | 8/2017 | |
| WO | WO 2018/064976 A1 | 4/2018 | |
| WO | WO 2018/143286 A1 | 8/2018 | |
| WO | WO 2018/232323 A1 | 12/2018 | |
| WO | WO 2019/230756 A1 | 12/2019 | |
| WO | WO 2020/203369 A1 | 10/2020 | |
| WO | WO 2020/203579 A1 | 10/2020 | |
| WO | WO-2020196678 A1 * | 10/2020 | ........... C12N 5/0697 |

OTHER PUBLICATIONS

BioLife Solutions "Understanding Temperature Ranges in Biological Storage", BioLife Solutions Inc., URL:www.biolifesolutions.com/blog/news/biological-material-storage-temperatures-ranges-explained/>, May 8, 2019, 4 pages. (Year: 2019).*
Bo-Wen Li et al., "Cryopreservation of Fat Tissue and Application in Autologous Fat Graft: In Vitro and In Vivo Study", Aesthetic Plastic Surgery, Springer-Verlag, NE, vol. 36, No. 3, Dec. 22, 2011, p. 714-p. 722, XP035058093.
Dong Yeon Kim et al., "Cryopreservation of lipoaspirates: in vitro measurement of the viability of adipose-derived stem cell and lipid peroxidation", International Wound Journal, vol. 17, No. 5, May 11, 2020, p. 1282-p. 1290, XP93143643.
Fiona Louis et al., "Bioprinted Vascularized Mature Adipose Tissue with Collagen Microfibers for Soft Tissue Regeneration", Cyborg and Bionic Systems, vol. 2021, Jan. 1, 2021, XP093095679, 15 pages.
Extended European Search Report issued in counterpart European Application No. 21885941.1 dated Apr. 8, 2024 , 10 pages.
English Translation of IPRP (PCT/IB/338 and PCT/IB/373) (May 11, 2023) and the Written Opinion of ISA (PCT/ISA/237) issued in International Application No. PCT/JP2021/035874 dated Dec. 21, 2021 (7 pages).
International Search Report issued in corresponding International Application No. PCT/JP2021/038303 dated Dec. 21, 2021.

* cited by examiner

*Primary Examiner* — Aaron J Kosar
(74) *Attorney, Agent, or Firm* — XSENSUS LLP

(57) ABSTRACT

The present invention relates to a method for freezing a cell structure including freezing a cell structure including fragmented extracellular matrix components, cells and fibrin and having a three-dimensional tissue structure.

19 Claims, 7 Drawing Sheets

(A) Live/Dead (B)

Day 0
200 μm
50 μm (A)

(B)

METHOD FOR FREEZING CELL STRUCTURE

CROSS REFERENCE TO RELATED APPLICATIONS

This application is a U.S. national stage of International Application No. PCT/JP2021/038303, filed on Oct. 15, 2021, which claims the priority benefit of Japanese Application No. 2020-181512, filed on Oct. 29, 2020. Both the International Application and the Japanese Application are incorporated by reference herein in their entirety.

TECHNICAL FIELD

The present invention relates to a method for freezing a cell structure.

BACKGROUND ART

As a method for artificially producing a structure imitating a living tissue, for example, a method for producing a three-dimensional tissue construct including three-dimensionally arranging cells coated with a collagen-containing coating to form a three-dimensional tissue construct (Patent Literature 1), a method for producing a three-dimensional cell tissue including mixing cells with a cationic substance and an extracellular matrix component to obtain a mixture, and collecting cells from the obtained mixture to form cell aggregates on a substrate (Patent Literature 2) and the like are known. In addition, the inventors have proposed a method for producing a large-sized three-dimensional tissue construct with a thickness of 1 mm or more with a relatively small number of cells by bringing fragmented exogenous collagen into contact with cells (Patent Literature 3). These three-dimensional tissue constructs are expected to be used as substitutes for experimental animals, materials for transplantation and the like.

CITATION LIST

Patent Literature

[Patent Literature 1] PCT International Publication No. WO2015/072164

[Patent Literature 2] PCT International Publication No. WO2017/146124

[Patent Literature 3] PCT International Publication No. WO2018/143286

SUMMARY OF INVENTION

Technical Problem

According to the method for producing a three-dimensional tissue construct described above, it is possible to obtain a cell structure which is an aggregate of cells artificially produced by cell culture. On the other hand, there is no known method for freezing a cell structure and maintaining the original function and/or structure of the cell structure.

An object of the present invention is to provide a method for freezing a cell structure that sufficiently maintains its function and/or structure even after thawing.

Solution to Problem

The present invention is based on new findings that, when a cell structure comprising fragmented extracellular matrix components, cells and fibrin, and having a three-dimensional tissue structure is frozen, the structure and/or function of the cell structure is maintained even after thawing.

The present invention relates to a method for freezing a cell structure comprising freezing a cell structure comprising fragmented extracellular matrix components, cells and fibrin and having a three-dimensional tissue structure.

The method for freezing a cell structure of the present invention comprises freezing a cell structure comprising fragmented extracellular matrix components, cells and fibrin and having a three-dimensional tissue structure, and thereby the function and/or structure of the cell structure is sufficiently maintained even after thawing.

The cell structure may have a vascular network between cells. In this case, the effects of the present invention are exhibited more significantly.

The cells may comprise at least adipocytes.

The method for freezing a cell structure of the present invention may further comprise maintaining the cell structure under a condition of −160° C. The method for freezing a cell structure of the present invention may further comprise maintaining the frozen cell structure in a frozen state for 7 days or longer.

The frozen cell structure may maintain the three-dimensional tissue structure and/or function after thawing. In addition, the ratio of the number of viable cells in the frozen cell structure after thawing to the number of viable cells in the cell structure before freezing may be 80% or more.

Advantageous Effects of Invention

According to the present invention, it is possible to provide a method for freezing a cell structure in which the function and/or structure is sufficiently maintained even after thawing.

BRIEF DESCRIPTION OF DRAWINGS

FIG. 1(A) shows the results of a cell structure in which no vascular network was formed between cells, and FIG. 1(B) shows images of the results of a cell structure in which a vascular network was formed between cells.

FIG. 4(A) shows the results obtained when Labobanker was used as a cryopreservation solution, and FIG. 4(B) shows the results obtained when a trehalose mixture was used as a cryopreservation solution.

DESCRIPTION OF EMBODIMENTS

Figure 1:
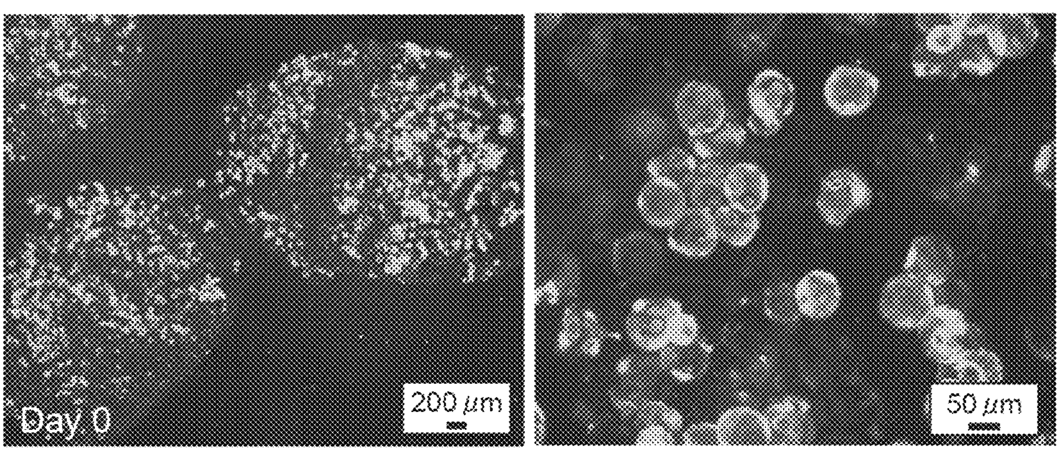
FIG. 1 shows images of the results of Live/Dead assay of a cell structure before freezing (day 0)

Hereinafter, forms for implementing the present invention will be described in detail. However, the present invention is not limited to the following embodiments.

A method for freezing a cell structure according to the present embodiment comprises freezing a cell structure comprising fragmented extracellular matrix components, cells and fibrin and having a three-dimensional tissue structure (freezing step).

In this specification, the "cell structure" is a cell aggregate (mass-like cell population) artificially produced by cell culture. In this specification, the "three-dimensional tissue structure" is a structure in which cells are three-dimensionally disposed via extracellular matrix components. The shape of the cell structure having a three-dimensional tissue structure is not particularly limited, and examples thereof include a sheet shape, a spherical shape, substantially a spherical shape, an ellipsoidal shape, substantially an ellipsoidal shape, a hemispherical shape, substantially a hemispherical shape, a semicircular shape, substantially a semicircular shape, a rectangular parallelepiped shape, and substantially a rectangular parallelepiped shape. Here, living tissue comprises sweat glands, lymphatic vessels, sebaceous glands, and the like, and has a more complex configuration than the cell structure. Therefore, the cell structure and living tissue can be easily distinguished.

(Cells)

In this specification, "cells" are not particularly limited, and for example, cells derived from mammals such as humans, monkeys, dogs, cats, rabbits, pigs, cows, mice, and rats may be used. The parts of cells derived are not particularly limited, and may be somatic cells derived from bones, muscles, internal organs, nerves, brain, bones, skin, blood, and the like or may be germ cells. In addition, the cells may be stem cells or may be cultured cells such as primary cultured cells, sub-cultured cells and cell line cells.

In this specification, the "stein cells" are cells having a self-replication ability and pluripotency. Stem cells include pluripotent stem cells having an ability to differentiate into any cell tumor and tissue stem cells (also called somatic stem cells) having an ability to differentiate into specific cell tumors. Examples of pluripotent stem cells include embryonic stem cells (ES cells), somatic cell-derived ES cells (ntES cells) and induced pluripotent stem cells (iPS cells). Examples of tissue stem cells include mesenchymal stem cells (for example, adipose stem cells and bone marrow-derived stem cells), hematopoietic stem cells and neural stem cells. Examples of adipose stem cells include human adipose-derived stem cells (ADSC).

The cells may comprise at least adipocytes. In this specification, "adipocytes" means all adipocytes other than adipose stem cells. Adipocytes include mature adipocytes and adipocytes that are not included in adipose stem cells, and the adipocytes preferably comprise mature adipocytes, and more preferably, 90% or more of a total number of adipocytes are mature adipocytes, and still more preferably, all of the adipocytes are mature adipocytes. For adipocytes, for example, cells collected from a subcutaneous adipose tissue, an epicardial-derived adipose tissue or the like may be used, and collected cells (for example, adipose stem cells) that are induced to differentiate may be used. Adipocytes are not particularly limited, but when an adipose tissue constructed from adipocytes is eventually used as a tissue at a specific site in a living body, it is preferable to use a component derived from the tissue corresponding to the tissue at that site.

The size of lipid droplets can be used as an index indicating the maturity of adipocytes. Lipid droplets are cell organelles that store lipids such as triglycerides (neutral fats) and cholesterol, and the lipids are covered with a single layer of phospholipids to have a droplet-like shape. In addition, expression of adipose tissue-specific proteins (perilipin, etc.) on the surface of the phospholipids is observed. Although the size of lipid droplets of mature adipocytes varies, for example, when the average value of lipid droplet sizes is 20 μm or more, it can be said that the adipocytes are mature to some extent, that is, the adipocytes are mature.

The content of adipocytes with respect to a total number of cells in the cell structure may be, for example, 5% or more, 10% or more, 15% or more, 20% or more, 25% or more, or 30% or more, and may be 95% or less, 90% or less, 80% or less or 75% or less.

The cells may further comprise vascular endothelial cells. In this specification, "vascular endothelial cells" are squamous cells constituting the surface of the intravascular lumen. Examples of vascular endothelial cells include human umbilical vein-derived vascular endothelial cells (HUVEC).

The content of vascular endothelial cells with respect to a total number of cells in the cell structure may be, for example, 5% or more, 10% or more, 15% or more, 20% or more, 25% or more or 30% or more, and may be 95% or less, 90% or less, 80% or less, or 75% or less.

Cells may comprise adipocytes and vascular endothelial cells. In addition to adipocytes and vascular endothelial cells, the cells may further comprise cells other than adipocytes and vascular endothelial cells. Examples of cells other than adipocytes and vascular endothelial cells include mesenchymal cells such as fibroblasts, chondrocytes, and osteoblasts, colon cancer cells (for example, human colon cancer cells (HT29)), cancer cells such as liver cancer cells, cardiomyocytes, epithelial cells (for example, human gingival epithelial cells), lymphatic endothelial cells, nerve cells, dendritic cells, hepatocytes, adherent cells (for example, immune cells), smooth muscle cells (for example, aortic smooth muscle cells (Aorta-SMC)), pancreatic islet cells, and keratinocytes (for example, human epidermal keratinocytes).

The ratio between the numbers of cells of adipocytes and vascular endothelial cells in the cell structure (adipocytes/vascular endothelial cells) is not particularly limited, and may be, for example, 100/1 to 1/100, 50/1 to 1/50, 20/1 to 1/1, 10/1 to 1/1, 8/1 to 1/1, 7/1 to 1.2/1, 6/1 to 1.5/1, 5/1 to 2/1 or 3/1 to 2/1.

The cell structure may have a vascular network between cells. When there is a vascular network between cells, the viability of cells in the cell structure after thawing tends to be even closer to the viability before freezing. In addition, when a vascular network is formed between cells, it is expected that the cell structure will be able to be maintained for a long period and the cell structure will be easily engrafted when transplanted to mammals and the like.

"Having a vascular network between cells" means having a structure in which branched blood vessels extend between cells so that they surround cells, similar to in living tissue. Whether a vascular network similar to that of a living tissue is formed can be determined based on, for example, the number of blood vessel branches in a living tissue and/or the length between blood vessel branches and/or the variability in diameter of the blood vessels. For example, when the average value of the number of blood vessel branches in the cell structure is 80% or more and 150% or less, 85% or more and 130% or less, or 90% or more and 120% or less of the average value of the number of blood vessel branches in living tissue, it may be determined to be similar to the number of blood vessel branches in living tissue. In addition, for example, when the average value of the number of blood vessel branches in the cell structure is 2.5 or more and 4.5 or less, or 3.0 or more and 4.2 or less, it may be determined to be similar to the number of blood vessel branches in living tissue. For example, when the average value of the length between blood vessel branches in the cell structure is 80% or more and 150% or less, 85% or more and 130% or less, and 90% or more and 120% or less of the average value of the length between blood vessel branches in living tissue, it may be determined to be similar to the length between blood vessel branches in living tissue. Both thick blood vessels and thin blood vessels are observed in living tissue. Here, for example, similar to living tissue, when both blood vessels with a large diameter (for example, 10 μm or more and less than 25 μm) and blood vessels with a small diameter (for example, more than 0 μm and less than 10 μm) are observed, it may be determined to have the same variability as that of the diameter of blood vessels in living tissue. In addition, for example, when 60% or more, 70% or more or 80% or more of the diameters of all blood vessels is distributed over more than 0 μm and less than 25 μm, it may be determined to have the same variability as that of the diameters of blood vessels in living tissue. When cells include adipocytes, the cell structure preferably has a vascular network between adipocytes. In this case, it is preferable not only to have a vascular network, but also adipocytes surrounded by blood vessels close to living tissue. For example, when the average value of lipid droplet sizes of adipocytes in the cell structure according to the present embodiment is 20 μm to 180 μm or 100 μm to 180 μm, the cell structure may be determined to have adipocytes similar to adipocytes in living tissue. When comparing living tissue and the cell structure, living tissue and the cell structure are compared under the same conditions (for example, per a certain volume, per a certain area in the case of image analysis, per a certain sample, etc.).

(Fragmented Extracellular Matrix Component)

Fragmented extracellular matrix components can be obtained by fragmenting extracellular matrix components. In this specification, the "extracellular matrix component" is an aggregate of extracellular matrix molecules formed by a plurality of extracellular matrix molecules. The extracellular matrix is a substance that is present outside cells in an organism. As the extracellular matrix, any substance can be used as long as it does not adversely affect cell growth and formation of cell aggregates. Specific examples include collagen, elastin, proteoglycan, fibronectin, hyaluronic acid, laminin, vitronectin, tenascin, entactin and fibrillin, but the present invention is not limited thereto. The extracellular matrix components may be used alone or may be used in combination. The extracellular matrix components may comprise, for example, collagen components, or may be collagen components. The extracellular matrix component in the present embodiment is preferably a substance present outside cells of an animal, that is, an extracellular matrix component of an animal.

The extracellular matrix molecule may be a modifier or variant of the above extracellular matrix molecule as long as it does not adversely affect the growth of cells and formation of cell aggregates, and may be a polypeptide such as a chemically synthesized peptide. The extracellular matrix molecule may have a repetition of a sequence represented by Gly-X-Y, which is a characteristic of collagen. Here, Gly represents a glycine residue, and X and Y each independently represent an arbitrary amino acid residue. A plurality of Gly-X-Y's may be the same as or different from each other. When a repetition of a sequence represented by Gly-X-Y is provided, there are few restrictions on the arrangement of molecular chains, and for example, the function as a scaffolding material during cell culture is further improved. In the extracellular matrix molecule having a repetition of a sequence represented by Gly-X-Y, the proportion of the sequence represented by Gly-X-Y may be 80% or more and preferably 95% or more of the complete amino acid sequence. In addition, the extracellular matrix molecule may be a polypeptide having an RGD sequence. The RGD sequence is a sequence represented by Arg-Gly-Asp (arginine residue-glycine residue-aspartic acid residue). For example, when the RGD sequence is provided, cell adhesion is further promoted, which makes it more suitable as a scaffolding material during cell culture. Examples of extracellular matrix molecules comprising a sequence represented by Gly-X-Y and an RGD sequence include collagen, fibronectin, vitronectin, laminin, and cadherin.

Examples of collagen include fibrous collagen and non-fibrous collagen. Fibrous collagen is collagen comprising collagen fibers as a main component, and specific examples thereof include type I collagen, type II collagen, and type III collagen. Examples of non-fibrous collagen include type IV collagen.

Examples of proteoglycans include chondroitin sulfate proteoglycan, heparan sulfate proteoglycan, keratan sulfate proteoglycan, and dermatan sulfate proteoglycan, but the present invention is not limited thereto.

The extracellular matrix component may comprise at least one selected from the group consisting of collagen, laminin and fibronectin, and preferably comprises collagen so that the effects of the present invention become more significant. Collagen is preferably fibrous collagen, and more preferably type I collagen. Regarding fibrous collagen, commercially available collagen may be used, and specific examples thereof include porcine skin-derived type I collagen (commercially available from NH Foods Ltd.).

The extracellular matrix component may be an animal-derived extracellular matrix component. Examples of animal species from which an extracellular matrix component is derived include humans, pigs, and cows, but the present invention is not limited thereto. Regarding the extracellular matrix component, a component derived from one kind of animal may be used, or a component derived from a plurality of kinds of animals may be used in combination.

"Fragmentation" means that aggregates of extracellular matrix molecules are made smaller in size. Fragmentation may be performed under conditions in which the bond within the extracellular matrix molecule breaks or may be performed under conditions in which the bond within the extracellular matrix molecule does not break. The fragmented extracellular matrix component may comprise an extracellular matrix component that has been defibrated (defibrated extracellular matrix component) which is a component obtained by defibrating the above extracellular matrix component by applying a physical force. Defibrillation is an aspect of fragmentation, and may be performed, for example, under conditions in which the bond within the extracellular matrix molecule does not break.

A method for fragmenting an extracellular matrix component is not particularly limited. Regarding a method for defibrating an extracellular matrix component, for example, an extracellular matrix component may be defibrated by applying a physical force with an ultrasonic homogenizer, a stirring homogenizer, a high pressure homogenizer or the like. When the stirring homogenizer is used, the extracellular matrix component may be homogenized directly or may be homogenized in an aqueous medium such as saline. In addition, a defibrated extracellular matrix component with a millimeter size or nanometer size can also be obtained by adjusting a homogenizing time, the number of times, and the like. The defibrated extracellular matrix component can also be obtained according to defibrating by repeating freezing and melting.

At least a part of the fragmented extracellular matrix component may comprise the defibrated extracellular matrix component. In addition, the fragmented extracellular matrix component may be composed of only the defibrated extracellular matrix component. That is, the fragmented extracellular matrix component may be a defibrated extracellular matrix component. The defibrated extracellular matrix component preferably comprises a defibrated collagen component (defibrated collagen component). The defibrated collagen component preferably maintains a triple helix structure derived from collagen. The defibrated collagen component may be a component that partially maintains a triple helix structure derived from collagen.

Examples of the shape of the fragmented extracellular matrix component include a fibrous form. The fibrous form means a shape composed of a filamentous collagen component or a shape composed of a filamentous extracellular matrix component crosslinked between molecules. At least a part of the fragmented extracellular matrix component may be fibrous. Examples of fibrous extracellular matrix components include fine filaments (fine fibers) formed by aggregating a plurality of filamentous extracellular matrix molecules, filaments formed by additionally aggregating fine fibers, and those obtained by defibrating these filaments. The fibrous extracellular matrix component can retain the RGD sequence without disruption.

The average length of the fragmented extracellular matrix components may be 100 nm or more and 400 μm or less or 100 nm or more and 200 μm or less. In one embodiment, the average length of the fragmented extracellular matrix components may be 5 μm or more and 400 μm or less, 10 μm or more and 400 μm or less, 22 μm or more and 400 μm or less, or 100 μm or more and 400 μm or less. In another embodiment, in order to further improve redispersibility, the average length of the fragmented extracellular matrix components may be 100 μm or less, 50 μm or less, 30 μm or less, 15 μm or less, 10 μm or less, 1 μm or less, or 100 nm or more. The average length of most of the fragmented extracellular matrix components within all the fragmented extracellular matrix components is preferably within the above numerical value range. Specifically, the average length of 95% of the fragmented extracellular matrix components within all the fragmented extracellular matrix components is preferably within the above numerical value range. The fragmented extracellular matrix component is preferably a fragmented collagen component having an average length within the above range, and more preferably a defibrated collagen component having an average length within the above range.

The average diameter of the fragmented extracellular matrix components may be 10 nm or more and 30 μm or less, 30 nm or more and 30 μm or less, 50 nm or more and 30 μm or less, 100 nm or more and 30 μm or less, 1 μm or more and 30 μm or less, 2 μm or more and 30 μm or less, 3 μm or more and 30 μm or less, 4 μm or more and 30 μm or less, or 5 μm or more and 30 μm or less. The fragmented extracellular matrix component is preferably a fragmented collagen component having an average diameter within the above range, and more preferably a defibrated collagen component having an average diameter within the above range.

The average length and average diameter of the fragmented extracellular matrix components can be determined by measuring each fragmented extracellular matrix component under an optical microscope and performing image analysis. In this specification, the "average length" is an average value of the lengths of the measured samples in the longitudinal direction, and the "average diameter" is an average value of lengths of the measured samples in a direction orthogonal to the longitudinal direction.

The fragmented extracellular matrix component may comprise, for example, a fragmented collagen component, or may be composed of a fragmented collagen component. The "fragmented collagen components" are components which are obtained by fragmenting collagen components such as fibrous collagen components, and which maintain a triple helix structure. The average length of the fragmented collagen components is preferably 100 nm to 200 μm, more preferably 22 μm to 200 μm, and still more preferably 100 μm to 200 μm. The average diameter of the fragmented collagen components is preferably 50 nm to 30 μm, more preferably 4 μm to 30 μm, and still more preferably 20 μm to 30 μm.

At least some of the fragmented extracellular matrix components may be cross-linked intermolecularly or intramolecularly. The extracellular matrix components may be cross-linked within extracellular matrix molecules or between extracellular matrix molecules constituting the extracellular matrix components.

Examples of cross-linking methods include a physical cross-linking method by applying heat, ultraviolet rays, radiation, and the like, and a chemical cross-linking method using a cross-linking agent, an enzyme reaction and the like, and the method is not particularly limited. Physical cross-linking is preferable so that cell growth is not hindered. Cross-linking (physical cross-linking and chemical cross-linking) may be cross-linking via covalent bonds.

When the extracellular matrix components include collagen components, cross-links may be formed between collagen molecules (triple helix structure), and may be formed between collagen fibrils formed by collagen molecules. Cross-linking may be cross-linking by heat (thermal cross-linking). Thermal cross-linking can be performed, for example, by performing a heat treatment under a reduced pressure using a vacuum pump. When the collagen components are thermally cross-linked, the extracellular matrix components may be cross-linked when amino groups of collagen molecules form peptide bonds (—NH—CO—) with carboxyl groups of the same or other collagen molecules.

The extracellular matrix components can be cross-linked using a cross-linking agent. The cross-linking agent can, for example, cross-link carboxyl groups and amino groups, or can cross-link amino groups with each other. As the cross-linking agent, for example, an aldehyde-based, carbodiimide-based, epoxide-based or imidazole-based cross-linking agent is preferable in consideration of cost, safety and operability, and specific examples thereof include water-soluble carbodiimides such as glutaraldehyde, 1-ethyl-3-(3-dimethylaminopropyl)carbodiimide/hydrochloride, and 1-cyclohexyl-3-(2-morpholinyl-4-ethyl)carbodiimide/sulfonate.

The degree of cross-linking can be appropriately selected according to the type of the extracellular matrix components, a method for cross-linking, and the like. The degree of cross-linking may be 1% or more, 2% or more, 4% or more, 8% or more, or 12% or more, and may be 30% or less, 20% or less, or 15% or less. When the degree of cross-linking is within the above range, the extracellular matrix molecule can be appropriately dispersed, and the redispersibility after dry storage is favorable.

When amino groups in the extracellular matrix components are used for cross-linking, the degree of cross-linking can be quantified based on a TNBS (trinitrobenzenesulfonic acid) method. The degree of cross-linking by the TNBS method may be within the above range. The degree of cross-linking by the TNBS method is a proportion of amino groups used for cross-linking among amino groups of the extracellular matrix. When the extracellular matrix components include collagen components, the degree of cross-linking measured by the TNBS method is preferably within the above range.

The degree of cross-linking may be calculated by quantifying carboxyl groups. For example, in the case of extracellular matrix components that are insoluble in water, quantification may be performed by a TBO (toluidine blue O) method. The degree of cross-linking by the TBO method may be within the above range.

The content of the extracellular matrix component in the cell structure based on the cell structure (dry weight) may be 0.01 to 90 mass %, and is preferably 10 to 90 mass %, preferably 10 to 80 mass %, preferably 10 to 70 mass %, preferably 10 to 60 mass %, preferably 1 to 50 mass %, preferably 10 to 50 mass %, more preferably 10 to 30 mass %, and more preferably 20 to 30 mass %.

Here, the "extracellular matrix components in the cell structure" are extracellular matrix components constituting the cell structure, and may be derived from endogenous extracellular matrix components or may be derived from exogenous extracellular matrix components.

The "endogenous extracellular matrix components" are extracellular matrix components produced from extracellular matrix-producing cells. Examples of extracellular matrix-producing cells include mesenchymal cells such as the above fibroblasts, chondrocytes, and osteoblasts. The endogenous extracellular matrix components may be fibrous or non-fibrous.

The "exogenous extracellular matrix components" are extracellular matrix components supplied from the outside. The cell structure according to the present embodiment includes fragmented extracellular matrix components, which are exogenous extracellular matrix components. The exogenous extracellular matrix components may be the same as or different from endogenous extracellular matrix components of the animal species from which they are derived. Examples of the originating animal species include humans, pigs, and cows. In addition, the exogenous extracellular matrix components may be artificial extracellular matrix components.

When the extracellular matrix components are collagen components, the exogenous extracellular matrix components are also referred to as "exogenous collagen components," and the "exogenous collagen components," which are collagen components supplied from the outside, are aggregates of collagen molecules formed by a plurality of collagen molecules, and specific examples thereof include fibrous collagen and non-fibrous collagen. The exogenous collagen component is preferably fibrous collagen. The fibrous collagen is a collagen component which is a main component of collagen fibers, and examples thereof include type I collagen, type II collagen, and type Ill collagen. As the fibrous collagen, commercially available collagen may be used, and specific examples thereof include pig-skin-derived type I collagen (commercially available from NH Foods Ltd.). Examples of exogenous non-fibrous collagen include type IV collagen.

In the exogenous extracellular matrix components, the originating animal species may be different from that of the cells. In addition, when the cells include extracellular matrix-producing cells, in the exogenous extracellular matrix components, the originating animal species may be different from that of the extracellular matrix-producing cells. That is, the exogenous extracellular matrix components may be heterologous extracellular matrix components.

That is, when the cell structure includes endogenous extracellular matrix components and fragmented extracellular matrix components, the content of the extracellular matrix components constituting the cell structure is a total amount of the endogenous extracellular matrix components and the fragmented extracellular matrix components. The content of the extracellular matrix can be calculated from the volume of the obtained cell structure and the mass of the decellularized cell structure.

For example, when the extracellular matrix components comprised in the cell structure are collagen components, as a method for quantifying the amount of the collagen components in the cell structure, for example, the following method for quantifying hydroxyproline may be exemplified. A sample is prepared by mixing hydrochloric acid (HCl) with a dissolution solution in which a cell structure is dissolved, incubating at a high temperature for a predetermined time, and then returning the temperature to room temperature, and diluting a centrifuged supernatant to a predetermined concentration. A hydroxyproline standard solution is treated in the same manner as the sample, and then gradually diluted to prepare a standard. Each of the sample and the standard is subjected to a predetermined treatment with a hydroxyproline assay buffer and a detection reagent, and the absorbance at 570 nm is measured. The amount of the collagen components is calculated by comparing the absorbance of the sample with that of the standard. Here, the cell structure may be directly suspended in high-concentration hydrochloric acid, and the dissolution solution in which the cell structure is dissolved may be centrifuged to recover the supernatant, which is used for quantifying the collagen components. In addition, the cell structure to be dissolved may be in a state in which it is recovered from the culture solution without change, or the cell structure may be dissolved when a drying treatment is performed after recovering and liquid components are removed. However, when the cell structure that is recovered from the culture solution is dissolved and the collagen components are quantified, since the measured value of the weight of the cell structure is expected to vary due to the influence of the medium component absorbed by the cell structure and the remaining medium due to the problem of the experimental technique, it is preferable to use the weight after drying as a reference in order to stably measure the weight of the structure and the amount of the collagen component per unit weight.

As a method for quantifying the amount of the collagen components, more specifically, for example, the following method may be exemplified.

(Preparation of Sample)

A total amount of the frozen and dried cell structure is mixed with 6 mol/L HCl, and incubated at 95° C. for 20 hours or more in a heat block, and the temperature is then returned to room temperature. After centrifuging at 13,000 g for 10 minutes, the supernatant of the sample solution is recovered. A sample is prepared by appropriately diluting with 6 mol/L HCl so that the result falls within a range of a calibration curve in the measurement to be described below and then performing dilution of 200 μL with 100 μL of ultrapure water. 35 μL of the sample is used.

(Preparation of Standard)

125 μL of a standard solution (1,200 μg/mL in acetic acid) and 125 μL of 12 mol/l HCl are put into a screw cap tube and mixed, and the mixture is incubated at 95° C. for 20 hours in a heat block, and the temperature is then returned to room temperature. After centrifuging at 13,000 g for 10 minutes, the supernatant is diluted with ultrapure water to prepare 300 μg/mL of S1, and S1 is gradually diluted to prepare S2 (200 μg/mL), S3 (100 μg/mL), S4 (50 μg/mL), S5 (25 μg/mL), S6 (12.5 μg/mL), and S7 (6.25 μg/mL). S8 (0 μg/mL) containing only 90 μL of 4 mol/l HCl is also prepared.

(Assay)

35 μL of the standard and the sample are put into plates (included in QuickZyme Total Collagen Assay kit, commercially available from QuickZyme Biosciences). 75 μL of an assay buffer (included in the above kit) is added to each well. The plate is closed with a seal and incubation is performed at room temperature while shaking for 20 minutes. The seal is removed, and 75 μL of a detection reagent (reagent A: B=30 μL: 45 μL, included in the above kit) is added to each well. The plate is closed with a seal, the solution is mixed with shaking, and incubation is performed at 60° C. for 60 minutes. Cooling is sufficiently performed on ice, the seal is removed, and the absorbance at 570 nm is measured. The amount of the collagen components is calculated by comparing the absorbance of the sample with that of the standard.

The collagen components in the cell structure may be determined by an area ratio or volume ratio thereof. "Determined by the area ratio or the volume ratio" means that, for example, the collagen components in the cell structure are made distinguishable from other tissue structures by a known staining method (for example, immunostaining using anti-collagen antibodies or Masson trichrome staining), and the ratio of the existence area of the collagen components in the entire cell structure is then calculated using observation with the naked eye, various microscopes, image analysis software and the like. When the components are determined by the area ratio, there is no limitation on which cross section or surface in the cell structure is used to determine the area ratio, and for example, when the cell structure is a spherical component or the like, the components may be determined using a cross-sectional view that passes through substantially a center thereof.

For example, when the collagen components in the cell structure are determined by the area ratio, the ratio of the area based on the total area of the cell structure is 0.01 to 99%, preferably 1 to 99%, preferably 5 to 90%, preferably 7 to 90%, preferably 20 to 90%, and more preferably 50 to 90%. The "collagen components in the cell structure" are as described above. The ratio of the area of the collagen components constituting the cell structure is a ratio of the area of the endogenous collagen components and the exogenous collagen components in combination. The obtained cell structure is stained with Masson trichrome, and the ratio of the area of the collagen components can be calculated, for example, as a ratio of the area of the collagen components stained with blue to the total area of the cross section that passes through substantially a center of the cell structure.

The residual ratio of the cell structure subjected to a trypsin treatment with a trypsin concentration of 0.25%, a temperature of 37° C., a pH of 7.4, and a reaction time of 15 minutes is preferably 70% or more, more preferably 80% or more, and still more preferably 90% or more. Such a cell structure is stable because it is unlikely to be decomposed by an enzyme during culture or after culture. The residual ratio can be calculated from, for example, the mass of the cell structure before and after the trypsin treatment.

The residual ratio of the cell structure subjected to a collagenase treatment with a collagenase concentration of 0.25%, a temperature of 37° C., a pH of 7.4, and a reaction time of 15 minutes may be 70% or more, and is more preferably 80% or more, and still more preferably 90% or more. Such a cell structure is stable because it is unlikely to be decomposed by an enzyme during culture or after culture.

The cell structure according to the present embodiment can be produced by, for example, a method comprising a culture step in which cells with which fragmented extracellular matrix components are brought into contact are cultured in the presence of fibrin.

The method may further comprise a contact step in which fragmented extracellular matrix components are brought into contact with cells before the culture step.

In the contact step, extracellular matrix components may be brought into contact with cells in an aqueous medium. When the fragmented extracellular matrix components are dispersed in an aqueous medium, they easily come into contact with cells in the aqueous medium, and can promote formation of the cell structure. Examples of the contact step include methods such as a method of mixing an aqueous medium comprising fragmented extracellular matrix components and an aqueous medium comprising cells, a method of adding cells to an aqueous medium comprising fragmented extracellular matrix components, a method of adding an aqueous medium comprising extracellular matrix components to a culture solution comprising cells, a method of adding cells to an aqueous medium comprising extracellular matrix components, and a method of adding extracellular matrix components and cells to an aqueous medium prepared in advance, but the present invention is not limited thereto.

The concentration of the fragmented extracellular matrix components in the contact step can be appropriately determined according to the shape and thickness of a desired cell structure, the size of the incubator and the like. For example, the concentration of the fragmented extracellular matrix components in the aqueous medium in the contact step may be 0.1 to 90 mass % or 1 to 30 mass %.

The amount of the fragmented extracellular matrix components in the contact step with respect to, for example, $1.0\times10^6$ cells, may be 0.1 to 100 mg, 0.5 to 50 mg, 0.8 to 25 mg, 1.0 to 10 mg, 1.0 to 5.0 mg, 1.0 to 2.0 mg, or 1.0 to 1.8 mg, may be 0.7 mg or more, 1.1 mg or more, 1.2 mg or more, 1.3 mg or more or 1.4 mg or more, and may be 7.0 mg or less, 3.0 mg or less, 2.3 mg or less, 1.8 mg or less, 1.7 mg or less, 1.6 mg or less or 1.5 mg or less.

In the contact step, the mass ratio of the fragmented extracellular matrix components to the cells (fragmented extracellular matrix components/cells) is preferably 1/1 to 1,000/1, more preferably 9/1 to 900/1, and still more preferably 10/1 to 500/1.

A method for producing a cell structure according to one embodiment may comprise mixing fibrinogen and thrombin simultaneously or separately in the contact step or after the contact step and before the culture step. When fibrinogen and thrombin are mixed, they react to form fibrin.

The method may further comprise a step of co-sedimenting fragmented extracellular matrix components and cells in the aqueous medium after the contact step and before the culture step. When such a step is performed, the distribution of fragmented extracellular matrix components and cells in the cell structure becomes more uniform. Specific methods are not particularly limited, and for example, a method of centrifuging a culture solution comprising fragmented extracellular matrix components and cells may be exemplified.

A method for culturing cells with which the fragmented extracellular matrix is brought into contact is not particularly limited, and an appropriate culture method can be performed according to the type of cells to be cultured. For example, the culture temperature may be 20° C. to 40° C., or 30° C. to 37° C. The pH of the medium may be 6 to 8, or 7.2 to 7.4. The culture time may be 1 day to 2 weeks, or 1 week to 2 weeks.

The incubator (support) used for culturing cells with which the fragmented extracellular matrix is brought into contact is not particularly limited, and may be, for example, a well insert, a low adhesive plate, or a plate having a bottom shape such as a U shape and a V shape. The cells may be cultured while adhered to the support or the cells may be cultured without being adhered to the support or may be separated from the support during culture and cultured. When the cells are cultured without being adhered to the support or are separated from the support during culture and cultured, it is preferable to use a plate having a bottom shape such as a U shape and a V shape that inhibits adhesion of the cells to the support or a low adsorption plate.

The medium is not particularly limited, and an appropriate medium can be selected according to the type of cells to be cultured. Examples of mediums include an Eagle's MEM medium, a DMEM, a Modified Eagle medium (MEM), a Minimum Essential medium, an RPMI, and a GlutaMax medium. The medium may be a medium to which serum is added or a serum-free medium. The medium may be a mixed medium in which two types of mediums are mixed.

The cell density in the medium in the culture step can be appropriately determined according to the shape and thickness of a desired cell structure, the size of the incubator, and the like. For example, the cell density in the medium in the culture step may be 1 to $10^8$ cells/mL or $10^3$ to $10^7$ cells/mL. In addition, the cell density in the medium in the culture step may be the same as the cell density in the aqueous medium in the contact step.

(Fibrin)

The cell structure according to the present embodiment comprises fibrin. Fibrin is a component produced by the action of thrombin on fibrinogen to release Aα chains, A chains from the N terminal of Bβ chains, and B chains. Fibrin is a polymer and is generally insoluble in water. Fibrin is formed by bringing fibrinogen into contact with thrombin.

The content of fibrin with respect to 100 parts by mass of the fragmented extracellular matrix components may be 3 parts by mass or more or 10 parts by mass or more and may be 50 parts by mass or less or 30 parts by mass or less.

The thickness of the cell structure is preferably 10 μm or more, more preferably 100 μm or more, and still more preferably 1,000 μm or more. Such a cell structure is a structure closer to that of a living tissue, and is suitable as a substitute for an experimental animal and a material for transplantation. The upper limit of the thickness of the cell structure is not particularly limited, and may be, for example, 10 mm or less, 3 mm or less, 2 mm or less, 1.5 mm or less, or 1 mm or less.

Here, the "thickness of the cell structure" is a distance between both ends in a direction perpendicular to the main surface when the cell structure is sheet-like or a rectangular parallelepiped. When the main surface is uneven, the thickness is a distance at the thinnest part of the main surface.

In addition, when the cell structure is spherical or substantially spherical, the thickness of the cell structure is the diameter of the cell structure. In addition, when the cell structure is ellipsoidal or substantially ellipsoidal, the thickness of the cell structure is the breadth of the cell structure. When the cell structure is substantially spherical or substantially ellipsoidal, and the surface is uneven, the thickness of the cell structure is a distance between two points where the straight line passing through the center of gravity of the cell structure and the surface intersect, and is the shortest distance.

In the freezing step, the cell structure is frozen. For example, the cell structure that is stored in a storage container may be frozen. As the storage container, various commercially available storage containers may be used. As the storage container, for example, a cryogenic tube can be used.

The cell structure may be frozen together with a cryoprotective agent. Examples of cryoprotective agents include dimethyl sulfoxide (DMSO), glycerol, polyethylene glycol, propylene glycol, glycerin, polyvinylpyrrolidone, sorbitol, dextran, and trehalose. The cell structure may be frozen together with a cryopreservation solution containing a cryoprotective agent. As the cryopreservation solution, for example, a commercially available cryoprotective agent may be used. Examples of commercially available cryopreservation solutions include LaboBanker (product name, commercially available from Tosc Co., Ltd.). For example, a mixture containing trehalose, dimethyl sulfoxide and fetal bovine serum (FBS) can also be used as a cryopreservation solution.

A method for freezing a cell structure is not particularly limited, and for example, slow freezing may be performed. The cell structure may be frozen by storing it in a freezer.

The method for freezing a cell structure according to the present embodiment may comprise maintaining the cell structure at a predetermined freezing temperature. The freezing temperature may be lowered gradually or in steps. The freezing temperature is, for example, a temperature at which cells can be frozen, and may be −80° C. or lower, or −160° C. or lower, or −160° C. The lower limit value of the freezing temperature is not particularly limited, and may be, for example, −210° C. or higher. In order for the effects of the present invention to be exhibited more significantly, the method for freezing a cell structure according to the present embodiment may comprise maintaining the cell structure under a condition of −160° C. The freezing temperature is, for example, a set temperature of the freezer.

The freezing step may comprise, in this order, maintaining the cell structure at a first freezing temperature and maintaining the cell structure at a second freezing temperature that is a temperature lower than the first freezing temperature. The first freezing temperature may be, for example, −60 to −100° C. or −80° C. The second freezing temperature may be, for example, −140° C. to −180° C. or −160° C.

The method for freezing a cell structure according to the present embodiment may comprise maintaining the frozen cell structure in a frozen state. The period during which the frozen cell structure remains in a frozen state (freezing period) may be, for example, 7 days or longer, 30 days or longer, or 180 days or longer. The upper limit of the freezing period is not particularly limited, and may be, for example, 360 days or shorter.

According to the method for freezing a cell structure of one embodiment, the frozen cell structure maintains the three-dimensional tissue structure and/or function after thawing. The three-dimensional tissue structure may be the shape of the cell structure and the vascular network. The function of the cell structure may be a blood vessel connection function, and in the case of a cell structure comprising adipocytes, may be a fatty acid uptake capacity, a metabolic function, a predetermined biological factor secretion function or the like. For example, after thawing, when it has the same or substantially the same shape as before freezing, it is determined that the three-dimensional tissue structure is maintained.

Examples of methods of thawing a frozen cell structure include a method of immersion in a heated aqueous medium (for example, a medium), a method of heating from the outside of a storage container, and a combination of these methods. Before the frozen cell structure is thawed, as necessary, the thawed cell structure may be washed. For example, washing may be performed using a physiological buffer solution (for example, PBS) or the like.

The temperature of the aqueous medium for immersion may be, for example, 4° C. to 50° C., 30° C. to 40° C., or 36° C. to 38° C. The thawing time may be, for example, 3 minutes or shorter or 1 minute or shorter.

In the method for freezing a cell structure according to the present embodiment, the ratio ($X_1/X_0$) of the number of viable cells ($X_1$) after the frozen cell structure is thawed to the number of viable cells ($X_0$) in the cell structure before freezing may be 80% or more. $X_1/X_0$ can be measured by the method described in examples.

In one embodiment, a method further comprising maintaining the frozen cell structure in a frozen state in addition to the above freezing step can also be called a cell structure cryopreservation method.

EXAMPLES

Hereinafter, the present invention will be described in more detail with reference to examples. However, the present invention is not limited to the following examples.

100 mg of a type I collagen sponge fragment derived from pig skin (commercially available from NH Foods Ltd.) was heated at 200° C. for 24 hours, and thus a collagen component of which at least a part was cross-linked (cross-linked collagen component) was obtained. Here, before and after heating at 200° C., no significant change in appearance was observed in the collagen. 50 mg of the cross-linked collagen component was put into a 15 mL tube, 5 mL of ultrapure water was added thereto, and the mixture was homogenized using a homogenizer (VH-10 commercially available from As One Corporation) for 6 minutes to defibrate the cross-linked collagen component.

Centrifuging was performed under a condition of 21° C. at 10,000 rpm for 10 minutes. The supernatant was suctioned, and collagen pellets were mixed with 5 mL of fresh ultrapure water to prepare a collagen solution. While the tube containing the collagen solution was kept on ice, an ultrasonic treatment was performed using a sonicator (VC50 commercially available from Sonics and Materials) at 100 V for 20 seconds, the sonicator was removed, and the tube containing the collagen solution was then cooled on ice for 10 seconds, which was repeated 100 times. After the ultrasonic treatment was performed 100 times, the collagen solution was filtered with a filter having a pore size of 40 un to obtain a dispersion solution containing a defibrated collagen component (CMF). The dispersion solution was freeze-dried by a conventional method to obtain a defibrated collagen component (CMF) as a dried product. The average length (length) of CMF was 14.8±8.2 μm (N=20).

The cells, reagents, preparation methods and the like used in the production of cell structures were as follows.

(Cells and Collagen)

human adipose tissue (derived from thigh) for obtaining primary human mature adipocytes and human adipose-derived stem cells (ADSC) (provided from University Hospital, Kyoto Prefectural University of Medicine)

human umbilical vein-derived vascular endothelial cells (HUVEC) (#C-2517A commercially available from Lonza K. K.)

(Reagent)

bovine pancreas-derived insulin (#11882 commercially available from Sigma)

bovine plasma-derived thrombin freeze-dried powder (#T4648 commercially available from Sigma)

*Clostridium histolyticum*-derived collagenase type I (#C0130 commercially available from Sigma)

bovine plasma-derived fibrinogen I-S type (commercially available from Sigma #F8630)

DMEM (high glucose, commercially available from Nacalai Tesque, Inc.)

EGM-2MV BulletKit with growth factors (#C-2517A commercially available from Lonza K. K.)

(Mediums and Various Solutions)

EGM-2 medium: obtained by mixing 500 mL of EBM-2 with EGM-2 supplement growth factors and storing it at 4° C.

10 mg/mL insulin stock solution: obtained by dissolving 100 mg of the bovine pancreas-derived insulin in 10 mL of a 1% glacial acetic acid solution (pH≤2) diluted with water, dispensing equal amounts into Eppendorf tubes and storing it at −20° C.

2 mg/mL collagenase solution: 2.5 g of BSA was mixed with 50 mL of a DMEM (0% FBS, 1% antibiotic). In order to digest all adipose tissues in the 6-well plate, 26 mg of collagenase type I was mixed with 13 mL of DMEM (0% FBS, 5% BSA, 1% antibiotic), the mixture was filtered through a filter having a pore size of 0.2 μm, and the resultant was used.

50 mg/mL fibrinogen stock solution: 50 mg of fibrinogen was weighed out in an Eppendorf tube, and 1 mL of a DMEM (0% FBS, 1% antibiotic) was immediately added. After the tube was manually shaken for mixing, the mixture was left in a water bath at 37° C. for 3 to 5 minutes and filtered through a filter having a pore size of 0.2 μm, and equal amounts thereof were dispensed into Eppendorf tubes and used.

202 U/mL thrombin stock solution: thrombin 202 U was weighed out in an Eppendorf tube, 1 mL of a DMEM (0% FBS, 1% antibiotic) was immediately added, and the mixture was left in a water bath at 37° C. for 3 to 5 minutes and dissolved. Then, the mixture was filtered through a filter having a pore size of 0.2 μm, and equal amounts thereof were dispensed into Eppendorf tubes and used.

(Production Method)

A human adipose tissue section was washed with PBS containing 5% antibiotics. 4 to 6 g of the tissue was split into 6 wells of a 6-well plate. In 2 mL of a 2 mg/mL collagenase solution, the sample was finely chopped into a size of about 1 to 3 mm using scissors and tweezers. After incubation at 37° C. and 230 rpm for 1 hour, the sample was mixed with a 10 mL pipette for 30 minutes. The lysate was filtered through an iron mesh filter having a pore size of 500 μm, 2 mL of a DMEM was added per well, all the digested cells were collected and then centrifuged at 200 g for 3 minutes at room temperature (15 to 25° C.). Mature adipocytes were included in the upper yellow oily layer, and adipose stem cells and blood cells were included in pellets. Using a long needle and a 10 mL syringe, the medium between the upper layer and the lower layer was aspirated and discarded, and the mature adipocytes included in the upper layer and the adipose stem cells and blood cells included in the lower layer were washed with 25 mL of PBS (5% BSA, 1% antibiotic) twice. During washing, centrifuging was performed in the same manner as described above, separation was performed into three layers: the upper layer and the lower layer, and the medium between the upper layer and the lower layer, and the medium between the upper layer and the lower layer was aspirated and discarded. After performing washing twice, washing with 25 mL of a DMEM was performed.

Only the upper layer including mature adipocytes was collected and dispensed into Eppendorf tubes. Nuclei were stained with Hoechst staining (Hoechst diluted 1,000-fold, staining for 15 minutes), and the number of cells on a Turker Burk hemacytometer was counted using a fluorescence microscope.

A pellet containing ADSC was suspended in 10 mL of a DMEM, seeded in a 10 cm dish, and sub-cultured. ADSCs were separated from the dish using trypsin/EDTA and suspended in 1 mL of the DMEM, and the number of cells was counted.

HUVECs (commercially available from Lonza K. K.) were suspended in 10 mL of a DMEM, seeded in a 10 cm dish and sub-cultured. HUVEC were separated from the dish using trypsin/EDTA and suspended in 1 mL of the DMEM, and the number of cells was counted.

<Production of Cell Structure>

Production Example 1

1 mg of CMF was weighed out, 100 μL of a DMEM was added thereto, and the mixture was gently mixed until only small CMF particles were observed. Centrifuging was performed at room temperature and 10,000 rpm for 1 minute, and the supernatant was aspirated to obtain a CMF pellet. 250,000 cells of ADSC and 125,000 cells of HUVEC (ADSC:HUVEC=2:1) were gently added onto the CMF pellet and centrifuged at room temperature and 3,500 rpm for 1 minute without mixing, and the supernatant was aspirated. 0.3 mg of fibrinogen (6 μL of a 50 mg/mL fibrinogen stock solution) was added and gently mixed with the cells and CMF. In addition, 300,000 cells of mature adipocytes were added and gently mixed. As necessary, a small amount of a DMEM was added, and a total amount was adjusted to 70 μL. Immediately, 0.15 U of thrombin (0.71 μL of a 202 U/mL thrombin stock solution) was added and mixed, and the mixture was then slowly seeded into Transwell placed on a 6-well adapter on a 6-well plate.

After incubation in an incubator at 37° C. for 1 hour to cause gelling, 12 mL of an EGM-2 medium containing insulin at a final concentration of 10 μg/mL was added. 12 mL of the medium was replaced every 2 to 3 days until day 7 of culture. Thereby, a cell structure including CMF, adipocytes, vascular endothelial cells and fibrin was obtained. The cell structure was substantially spherical and had a vascular network between cells.

Production Example 2

A cell structure including CMF, adipocytes and fibrin was obtained in the same manner as in Production Example 1 except that a total number of cells was left unchanged, and a mixture in which all cells were mature adipocytes was used. The cell structure was substantially spherical.

<Evaluation Method>

For the cell structures produced by the above method, the cell viability in the cell structure before and after freezing was quantified using Live/Dead (registered trademark) Viability assay kit (Molecular Probes (registered trademark), and Thermo Fisher Scientific, Whaltam, Massachusetts, USA). The cell structure to be evaluated for cell viability was washed once with PBS, and then stained with calcein and ethidium homodimer-1 at 37° C. for 45 minutes. The stained cell structure was imaged using an epifluorescence confocal quantitative image cytometer CQ1. After matching measurement conditions and procedures between samples, Z-stacks using maximum intensity projection were executed while maintaining the same exposure time and excitation power for each sample and time, and the evaluation results were obtained. The percentage of each stain was calculated and ImageJ software was used for projection analysis.

The cell structure was added to the cryopreservation solution shown below.

LaboBanker (commercially available from Tosc Co., Ltd.)

Mixture containing 6% trehalose, 4% DMSO and 90% FBS (hereinafter referred to as a "trehalose mixture")

A tube containing a cell structure and a cryopreservation solution was transferred into a freezing container in which controlled slow freezing (1-2° C./min) was possible and left at −80° C. for 48 hours. Then, the tube was put into a deep freezer (Nihon Freezer, Osaka, Japan) and stored at −160° C. After 7 days and 30 days of storage, the frozen cell structure was washed in warm PBS, and then added to a DMEM at 37° C. and kept for 60 minutes, and thus thawed. Then, the sample was incubated in warm PBS containing a Live/Dead assay reagent for 45 minutes, and the cell viability was evaluated.

Live/Dead images were obtained using an epifluorescence confocal quantitative image cytometer CQ1. After matching measurement conditions and procedures between samples, Z-stacks using maximum intensity projection were executed while maintaining the same exposure time and excitation power for each sample and time, and the evaluation results were obtained. ImageJ software was used to analyze projection images, and the percentage of each staining was calculated.

For function evaluation, cell structures thawed after 30 days of cryopreservation in a deep freezer were used. Four of the thawed cell structures were put into the same wells in a 24-well plate (EZ-BindShut (trademark) II flat bottom) together with an EGM-2 medium containing 10 μg/mL of insulin, and the medium was replaced every 2-3 days. After the thawed cell structures were cultured for 7 days, it was confirmed whether the cell structures were fused between cell structures. Vascular attachment was evaluated according to NileRed lipid staining and counterstaining with Hoechst, and CD31 immunostaining.

In order to monitor fatty acid uptake by adipocytes, first, a substantially spherical cell structure was cultured in a DMEM medium containing only 1% of BSA and containing no glucose and FBS for 6 hours and put into a starvation state.

Then, 4 μM fluorescently labeled fatty acid analogs, BODIPY (trademark) 500/510C1, C12 were added to a medium containing 10 sg/mL of insulin for 60 minutes, and fatty acid uptake was induced. Fatty acid uptake was evaluated by counterstaining with Hoechst and propidium iodide (PI).

Under a condition of 37° C., viable cells were imaged using the confocal quantitative image cytometer CQ1. After matching measurement conditions and procedures between samples, Z-stacks using maximum intensity projection were executed while maintaining the same exposure time and excitation power for each sample and time, and the evaluation results were obtained.

<Evaluation Results>

Figure 2:
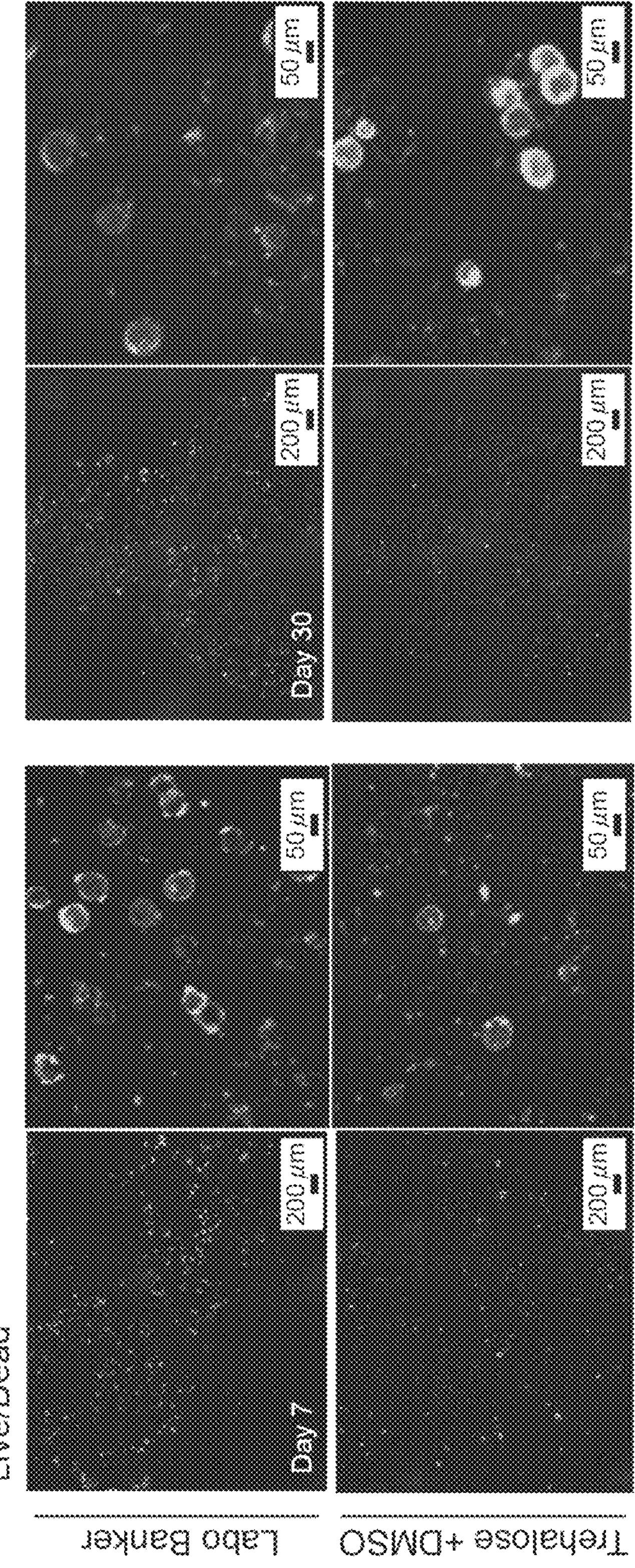
FIG. 2 shows images of the results of Live/Dead assay of cell structures cryopreserved for 7 days or 30 days.
Figure 3:
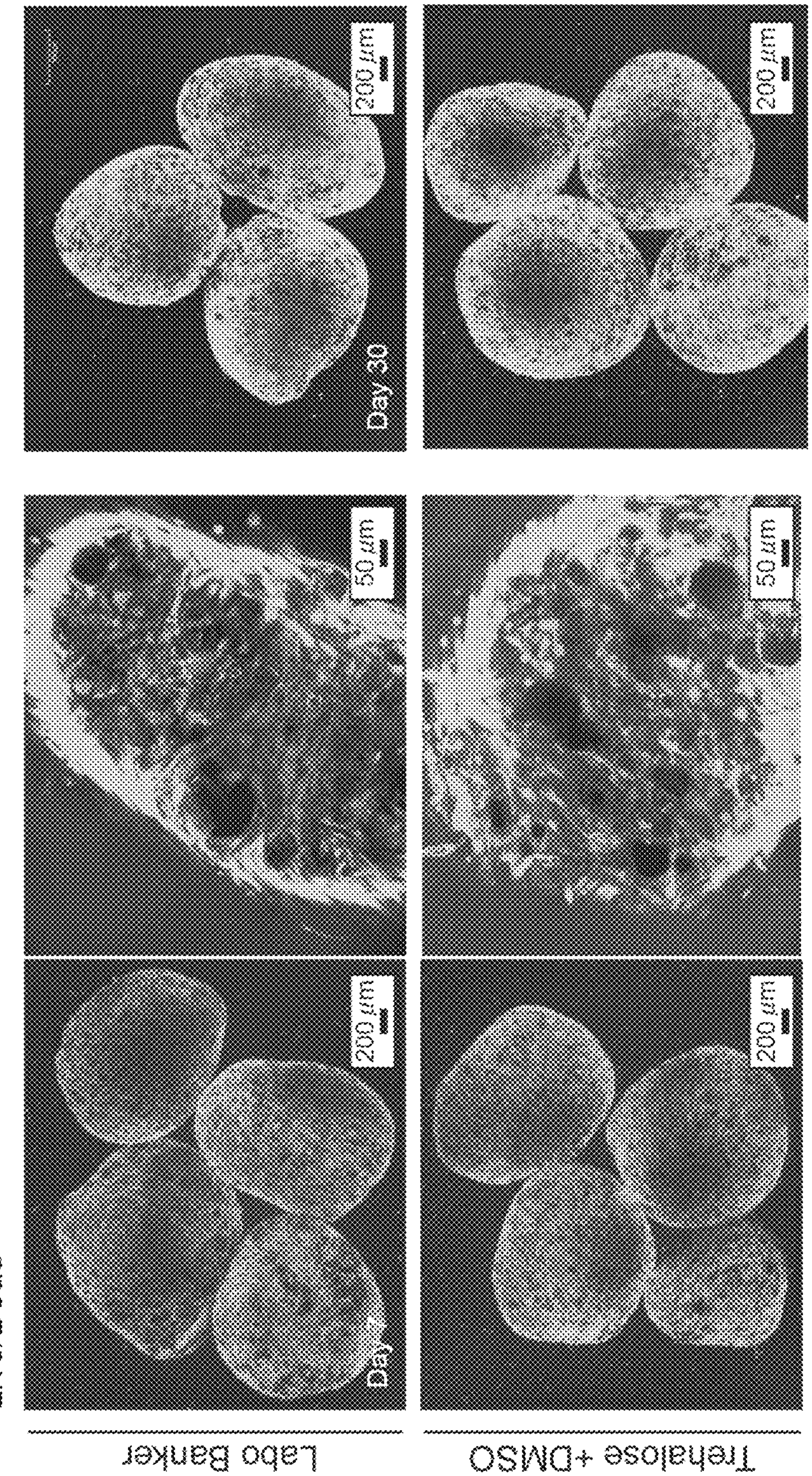
FIG. 3 shows images of the results of Live/Dead assay of cell structures cryopreserved for 7 days or 30 days.

FIGS. 1 to 3 show images of the results of Live/Dead assay using the cell structures of Production Example 1 and Production Example 2. FIG. 1 shows microscopic images of the evaluation results using the cell structure before freezing (day 0). FIG. 1(A) shows the results of cell structure (Production Example 2) including CMF, adipocytes and fibrin and having no vascular network, and FIG. 1(B) shows the results of the cell structure (Production Example 1) including CMF, adipocytes, vascular endothelial cells and fibrin and having a vascular network. FIGS. 2 and 3 show microscopic images of the evaluation results of the cell structures cryopreserved for 7 days or 30 days using Labobanker or a trehalose mixture as a cryopreservation solution, and FIG. 2 and FIG. 3 show the results of the cell structures of Production Example 2 and Production Example 1.

As shown in FIGS. 1 to 3, in both the cell structures of Production Example 1 and Production Example 2, it was confirmed that, even after cryopreservation and then thawing, the three-dimensional tissue structure (having substantially a spherical shape) was maintained, and cells in the cell structure were viable.

FIG. 4(A) and FIG. 4(B) show graphs of the results of cell viability in the cell structure of Production Example 1 during cryopreservation periods of 0 days, 7 days and 30 days. FIG. 4(A) shows the results obtained when Labobanker was used as a cryopreservation solution, and FIG. 4(B) shows the results obtained when a trehalose mixture was used as a cryopreservation solution. In FIG. 4(A) and FIG. 4(B), the results of the graphs show average value±standard deviation. Measurement was performed on images (n=4 to 6) per sample.

Figure 4:
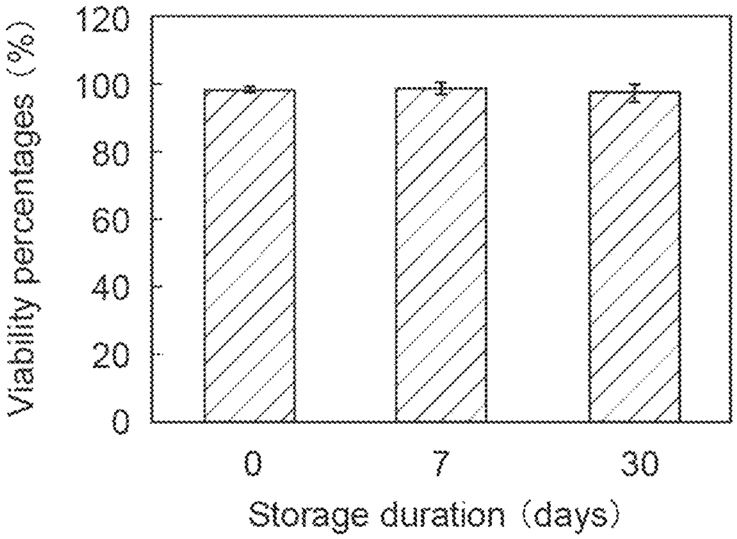
FIG. 4 shows graphs of the evaluation results of number of viable cells in cell structures cryopreserved for 0 days, 7 days or 30 days.
Figure 4:
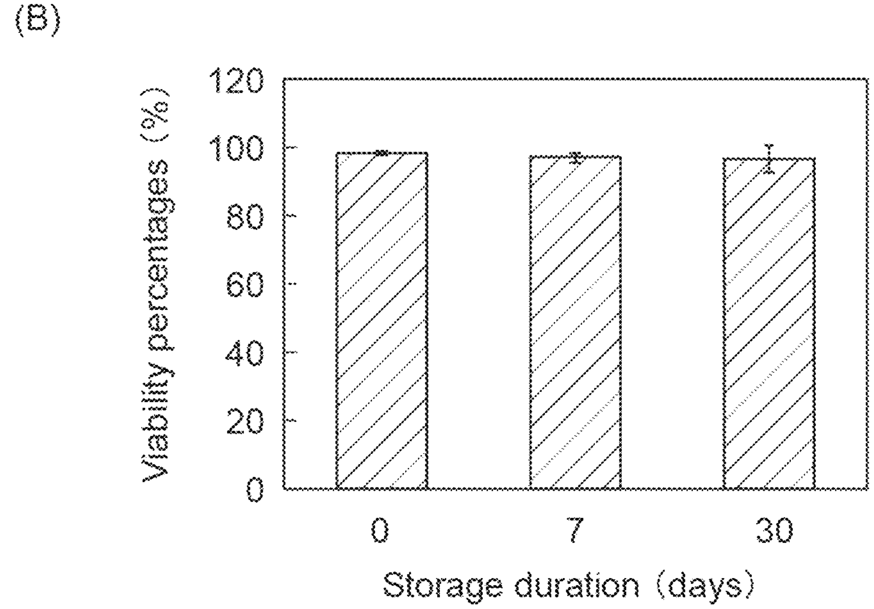

As shown in FIG. 4, the cell structure of Production Example 1 exhibited a high cell viability even after cryopreservation for 7 days and 30 days. There was no significant difference in cell viability in the cell structure between post-cryopreservation and pre-cryopreservation (day 0).

It was found that, when SDSC and HUVEC were used as cells in the cell structure, an effect of further improving the tissue viability after cryopreservation was obtained.

Figure 5:
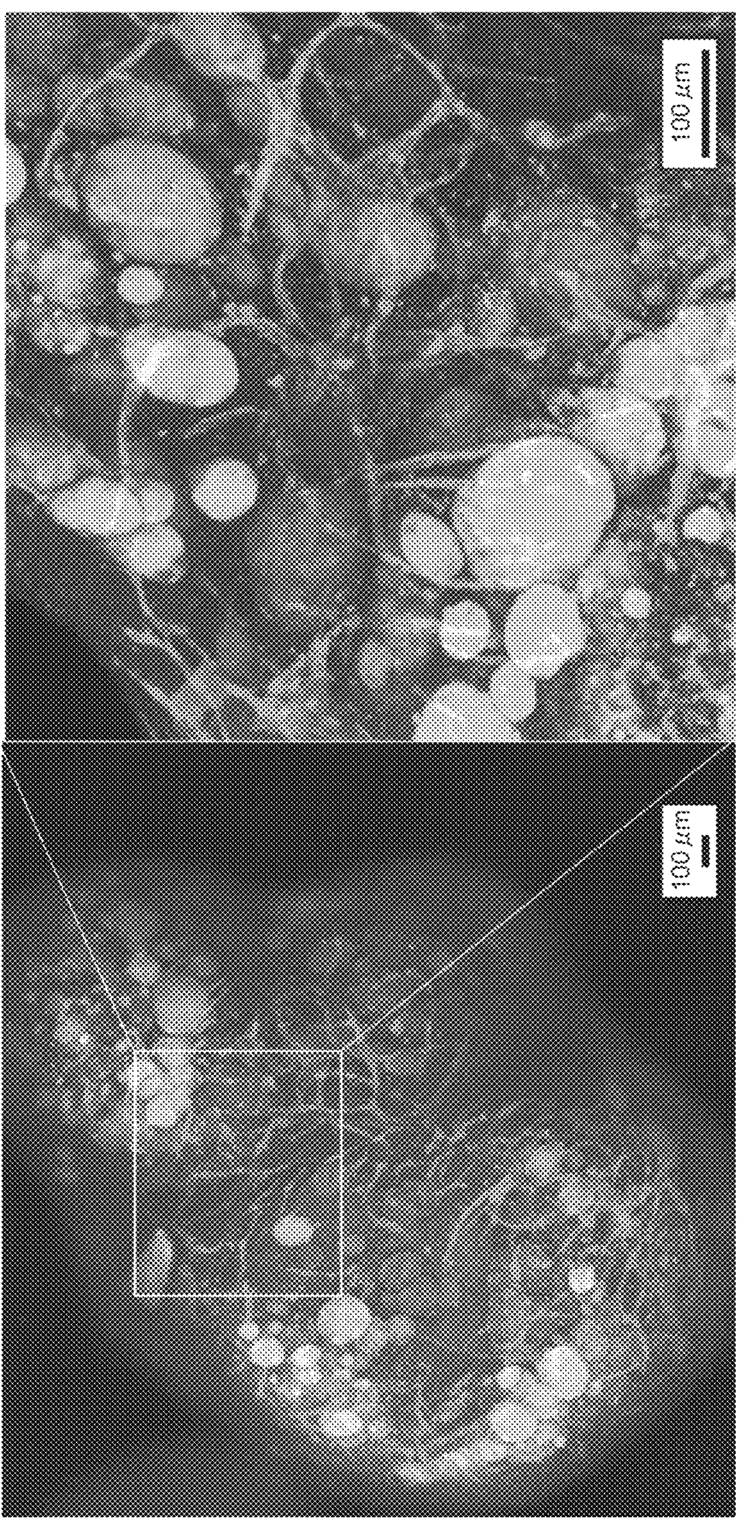
FIG. 5 shows images of the results obtained by evaluating a blood vessel connection function of a cell structure having a vascular network.
Figure 6:
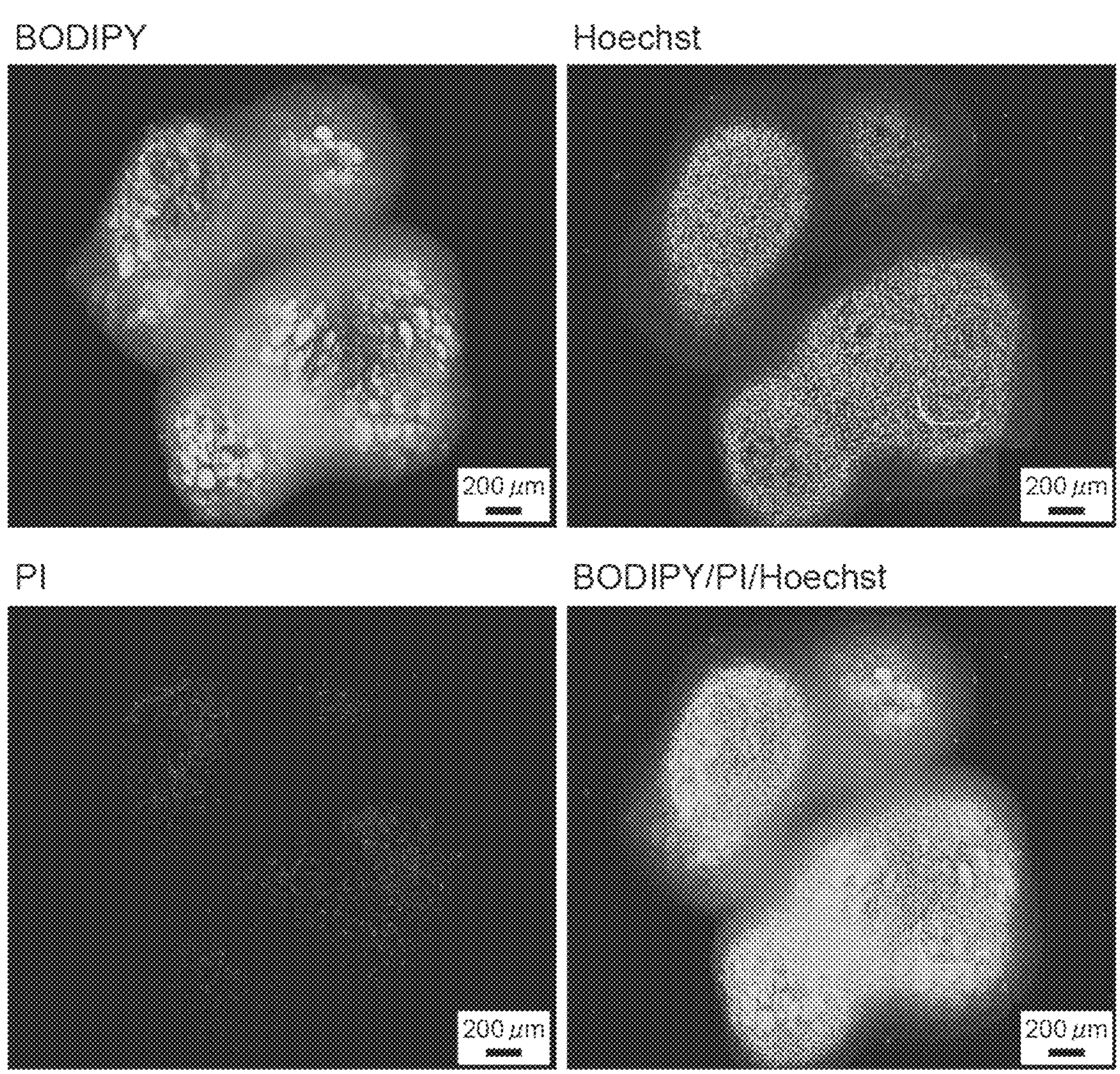
FIG. 6 shows images of the results obtained by evaluating a fatty acid uptake capacity of cell structures comprising adipocytes.

FIG. 5 and FIG. 6 are images showing the results obtained by confirming that the functionality of the cell structure after cryopreservation, particularly, the function of mature adipocytes after cryopreservation was maintained.

FIG. 5 shows images of the results obtained when samples obtained by cryopreservating a plurality of cell structures for 30 days, then performing thawing and then performing culturing in the same wells for 7 days were immunostained with NileRed and CD31. As shown in FIG. 5, the fusing ability of cell structures was confirmed when a plurality of cell structures were cultured in the same wells for 1 week even after 30 days of cryopreservation. In addition, vascular attachment between cell structures was also confirmed.

FIG. 6 shows cell structures counterstained with Hoechst and propidium iodide (PI), and shows images of the results of function evaluation of fatty acid uptake in mature adipocytes after insulin was introduced using BODIPY (trademark) 500/510C1, C12. Evaluation was performed with cell structures (n=4)/3 samples per well and condition.

FIG. 6 shows the results obtained by monitoring fatty acid uptake, which is one function of mature adipocytes, using fluorescently labeled fatty acid dodecanoic acid ($C_{12}H_{24}O_2$) analogs (BODIPY™ 500/510 C1, C12) after insulin was introduced, and in this non-invasive assay, fatty acid accumulation was evaluated in unilocular intracellular lipid vesicles after 60 minutes.

The above results showed that, in order to provide a stock that can be used to re-adjust the graft volume injected by subsequent injections depending on the result of volume loss, it may be possible to preserve the adipocyte tissue structure constructed according to a single liposuction procedure for patients.

Figure 7:
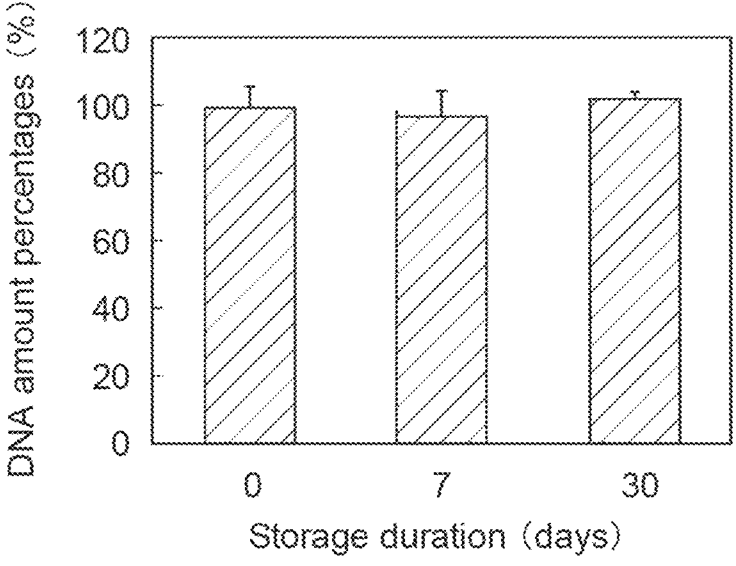
FIG. 7 is a graph showing the measurement results of the amount of DNA in cell structures (fat balls) comprising adipocytes.

As shown in FIG. 7, it was suggested that the amount of DNA did not change depending on the cryopreservation period (0 days, 7 days and 30 days), that is, the quality was maintained. Regarding the amount of DNA that was not changed, there was no difference due to the cryopreservation solution, and both the trehalose mixture and the Labobanker solution showed the same results.

The invention claimed is:

1. A method for cryopreserving cell structure, comprising freezing a cell structure comprising fragmented extracellular matrix components, cells and fibrin and having a three-dimensional tissue structure, wherein the cell structure has a fatty acid uptake function, a metabolic function, or a predetermined biological factor secretion function, wherein the cell structure includes a vascular network between the cells, and wherein the cells comprise at least adipocytes and adipose-derived stem cells.

2. The method for cryopreserving cell structure according to claim 1, comprising maintaining the cell structure under a condition of −160° C.

3. The method for cryopreserving cell structure according to claim 1, further comprising maintaining the frozen cell structure in a frozen state for 7 days or longer.

4. The method for freezing a cell structure according to claim 3, wherein the maintaining the frozen cell structure in a frozen state is for 30 days or longer.

5. The method for cryopreserving cell structure according to claim 1, thawing the frozen cell structure to obtain a thawed cell structure that maintains the three-dimensional tissue structure and/or a function after thawing.

6. The method for cryopreserving cell structure according to claim 5, wherein the ratio of the number of viable cells in the frozen cell structure after the thawing to the number of viable cells in the cell structure before freezing is 80% or more.

7. The method for cryopreserving cell structure according to claim 1, wherein the fragmented extracellular matrix components are defibrated collagen components.

8. The method for cryopreserving cell structure according to claim 1, wherein 90% or more of a total number of the adipocytes are mature adipocytes.

9. The method for cryopreserving cell structure according to claim 1, wherein the fragmented extracellular matrix components have an average length of 100 nm or more and 400 μm or less.

10. The method for freezing a cell structure according to claim 1, wherein the fragmented extracellular matrix components have an average diameter 10 nm or more and 30 μm or less.

11. The method for freezing a cell structure according to claim 1, wherein the fragmented extracellular matrix components are collagen components having a triple helix structure.

12. The method for freezing a cell structure according to claim 1, wherein the cell structure additionally comprises endogenous extracellular matrix components.

13. The method for freezing a cell structure according to claim 1, wherein the cell structure additionally comprises exogenous extracellular matrix components.

14. The method for freezing a cell structure according to claim 1, wherein the fibrin has a content with respect to 100 parts by mass of the fragmented extracellular matrix components of 3 parts by mass or more and 50 parts by mass or less.

15. The method for freezing a cell structure according to claim 1, wherein the cell structure has a thickness of 1,000 μm or more and 1 mm or less.

16. The method for freezing a cell structure according to claim 1, wherein the freezing comprises maintaining the cell structure at a first freezing temperature and maintaining the cell structure at a second freezing temperature, wherein the second freezing temperature is lower than the first freezing temperature.

17. The method for freezing a cell structure according to claim 1, wherein the first freezing temperature is −60° C. to −100° C. and the second freezing temperature is −140° C. to −180° C.

18. The method for freezing a cell structure according to claim 1, wherein the cell structure is spherical or substantially spherical.

19. A method for freezing a cell structure, comprising freezing a cell structure comprising fragmented extracellular matrix components, cells and fibrin and having a three-dimensional tissue structure, and thawing the frozen cell structure to obtain a thawed cell structure that maintains a function after thawing, wherein the function is a blood vessel connection function.

* * * * *